United States Patent
Ishiguro et al.

(10) Patent No.: US 10,816,413 B2
(45) Date of Patent: Oct. 27, 2020

(54) CALORIFIC VALUE MEASURING DEVICE AND CALORIFIC VALUE MEASURING METHOD

(71) Applicant: RIKEN KEIKI CO., LTD., Tokyo (JP)

(72) Inventors: Tomoo Ishiguro, Kasukabe (JP); Kenichi Kojima, Kasukabe (JP)

(73) Assignee: RIKEN KEIKI CO., LTD., Tokyo (JP)

( * ) Notice: Subject to any disclaimer, the term of this patent is extended or adjusted under 35 U.S.C. 154(b) by 426 days.

(21) Appl. No.: 15/580,162

(22) PCT Filed: Jun. 9, 2016

(86) PCT No.: PCT/JP2016/067206
§ 371 (c)(1),
(2) Date: Dec. 6, 2017

(87) PCT Pub. No.: WO2016/199849
PCT Pub. Date: Dec. 15, 2016

(65) Prior Publication Data
US 2018/0180493 A1  Jun. 28, 2018

(30) Foreign Application Priority Data
Jun. 11, 2015  (JP) .................... 2015-118171

(51) Int. Cl.
*G01K 17/04* (2006.01)
*G01N 29/024* (2006.01)
(Continued)

(52) U.S. Cl.
CPC ............ *G01K 17/04* (2013.01); *G01K 17/00* (2013.01); *G01K 17/06* (2013.01); *G01N 25/20* (2013.01);
(Continued)

(58) Field of Classification Search
CPC ........ G01K 17/00; G01K 17/04; G01K 17/06; G01N 21/3504; G01N 21/4133;
(Continued)

(56) References Cited

U.S. PATENT DOCUMENTS 6,279,380 B1 * 8/2001 Van Wesenbeeck ..................... G01N 33/225 73/23.31
6,286,360 B1 * 9/2001 Drzewiecki ............ A61B 5/083 702/24
(Continued)

FOREIGN PATENT DOCUMENTS

JP  2010175261 A  8/2010
WO  2012066828 A1  5/2012

OTHER PUBLICATIONS

English machine translation of WO2012/066828 (Year: 2012).*
(Continued)

*Primary Examiner* — Roy Y Yi
*Assistant Examiner* — Geoffrey T Evans
(74) *Attorney, Agent, or Firm* — Lucas & Mercanti, LLP

(57) ABSTRACT

It is an object of the present invention to provide a calorific value measuring device and a calorific value measuring method which enable highly reliable measurement of the calorific value of a by-product gas produced in a steelmaking process. In the present invention, with a by-product gas produced in a steelmaking process being employed as an object gas of which calorific value is to be measured, the refractive index and the sonic speed of the by-product gas are measured so as to compute a refractive index equivalent calorific value $Q_O$ from the value of the refractive index as well as a sonic speed equivalent calorific value $Q_S$ from the value of the sonic speed. On the basis of the concentration (Continued)

$X_{CO}$ of carbon monoxide gas contained in the by-product gas, an error calorific value $Q_{CO}$ is computed by Equation (1) below using a value selected within a range of −0.08 to −0.03 as a calorific value equivalent coefficient $\zeta$. On the basis of the refractive index equivalent calorific value $Q_O$, the sonic speed equivalent calorific value $Q_S$ and the error calorific value $Q_{CO}$ which have been computed, the calorific value Q of the by-product gas is determined by Equation (2) below using a value selected within a range of 1.1 to 4.2 as a correction factor $\alpha$.

$$Q_{CO} = X_{CO} \cdot \zeta \qquad \text{Equation (1)}$$

$$Q = Q_0 - \frac{Q_0 - Q_S}{1 - \alpha} - Q_{CO} \qquad \text{Equation (2)}$$

4 Claims, 2 Drawing Sheets

(51) Int. Cl.
- *G01N 33/22* (2006.01)
- *G01N 21/3504* (2014.01)
- *G01N 21/41* (2006.01)
- *G01K 17/00* (2006.01)
- *G01N 25/20* (2006.01)
- *G01K 17/06* (2006.01)

(52) U.S. Cl.
CPC ......... *G01N 29/024* (2013.01); *G01N 33/225* (2013.01); *G01N 21/3504* (2013.01); *G01N 21/4133* (2013.01); *G01N 2291/011* (2013.01); *G01N 2291/021* (2013.01)

(58) Field of Classification Search
CPC ....... G01N 2291/011; G01N 2291/021; G01N 25/20; G01N 29/024; G01N 33/225
See application file for complete search history.

(56) References Cited

U.S. PATENT DOCUMENTS

| | | | |
|---|---|---|---|
| 10,132,746 B2* | 11/2018 | Kojima | G01N 33/225 |
| 2002/0124630 A1* | 9/2002 | Jaeschke | G01N 33/225 |
| | | | 73/23.2 |
| 2004/0195531 A1* | 10/2004 | Rahmouni | G01N 33/225 |
| | | | 250/573 |
| 2013/0233056 A1* | 9/2013 | Ishiguro | G01N 9/00 |
| | | | 73/30.01 |
| 2014/0262836 A1* | 9/2014 | Liu | G01N 21/3504 |
| | | | 205/785.5 |

OTHER PUBLICATIONS

N. Nakamura, et al; Genba Kadai o Kaiketsu suru Opt-Sonic Netsuryokei no Kaihatsu to Kensho Kekka; Keiso; Nov. 2014; vol. 57; No. 11; pp. 21-24.

D. Iwamura; Zatsu Gas Seibun no Eikyo o Jokyo suru Netsuryokei; Keiryo Gijutsu; 2014; vol. 42; No. 8; pp. 44-46.

International Search Report dated Jul. 12, 2016 for PCT/JP2016/067206.

* cited by examiner

CALORIFIC VALUE MEASURING DEVICE AND CALORIFIC VALUE MEASURING METHOD

CROSS REFERENCE TO RELATED APPLICATION

This Application is a 371 of PCT/JP2016/067206 filed on Jun. 9, 2016 which, in turn, claimed the priority of Japanese Patent Application No. 2015-118171 filed Jun. 11, 2015, both applications are incorporated herein by reference.

TECHNICAL FIELD

The present invention relates to a calorific value measuring device and a calorific value measuring method which employ, for example, as a calorific value measurement object gas, a by-product gas such as a coke oven gas (COG), a blast furnace gas (BFG) and a Linz-Donawitz converter gas (LDG), produced in a steelmaking process.

BACKGROUND ART

The by-product gases produced in the steelmaking process, such as the coke oven gas (COG), the blast furnace gas (BFG) and the Linz-Donawitz converter gas (LDG), contain a flammable gas component such as hydrogen gas, carbon monoxide gases or methane gas. Thus, these by-product gases are reused, for example, as a fuel gas either singly or in combination of multiple sorts thereof. On the other hand, since the calorific value of a by-product gas is less than that of a typical fuel gas, a fuel gas having a calorific value greater than that of a by-product gas may be mixed to adjust the calorific value of a mixture gas to be obtained.

Then, to reuse the by-product gas as a fuel gas, it is necessary to grasp the calorific value of each by-product gas and the calorific value of the mixture gas.

Currently, for example, disclosed in Patent Literature 1 as a method for measuring the calorific value of a fuel gas is a calorific value measuring method which employs, as a calorific value measurement object gas, a gas that is predominantly composed of at least one sort of a paraffinic hydrocarbon gas and hydrogen gas and contains at least one sort of carbon dioxide gas, carbon monoxide gas, nitrogen gas and oxygen gas. More specifically, disclosed in Patent Literature 1 is that on the basis of the refractive index equivalent calorific value acquired from the refractive index of a calorific value measurement object gas and the density equivalent calorific value acquired from the density of the calorific value measurement object gas, the calorific value of the calorific value measurement object gas is computed by a specific relational equation using a value selected as a correction factor within a specific range.

CITATION LIST

Patent Literature

Patent Literature 1: Japanese Patent Application Laid-Open No. 2010-175261

SUMMARY OF INVENTION

Technical Problem

Then, for each miscellaneous gas other than a paraffinic hydrocarbon gas, the calorific value measuring method disclosed in Patent Literature 1 takes advantage of the fact that the ratio (correction factor) of a densimeter error to a refractometer error takes on a value (generally constant value) within a specific range irrespective of a sort of the gas, thus compensating a measurement error occurring in each of the refractive index equivalent calorific value and the density equivalent calorific value caused by the miscellaneous gas.

However, it was made clear that there occurred a measurement error when the calorific value of a by-product gas such as the coke oven gas (COG), the blast furnace gas (BFG) and the Linz-Donawitz converter gas (LDG), which are produced in a steelmaking process was measured by the method disclosed in Patent Literature 1.

The present invention has been made in view of the foregoing circumstances and provides, as its object, a calorific value measuring device and a calorific value measuring method which enable highly reliable measurement of the calorific value of a by-product gas produced in a steelmaking process.

Solution to Problem

A calorific value measuring device of the present invention is to measure a calorific value of a by-product gas produced in a steelmaking process and characterized by including:

a refractive index equivalent calorific value computation mechanism for computing a refractive index equivalent calorific value $Q_O$ [MJ/Nm$^3$] on the basis of the refractive index of the by-product gas that is a calorific value measurement object gas;

a sonic speed equivalent calorific value computation mechanism for computing a sonic speed equivalent calorific value $Q_S$ [MJ/Nm$^3$] on the basis of the sonic speed of the by-product gas;

an error calorific value measuring mechanism for computing an error calorific value $Q_{CO}$ [MJ/Nm$^3$] by Equation (1) below on the basis of the concentration $X_{CO}$ [vol % (volume percentage)] of carbon monoxide gas contained in the by-product gas using a value selected within a range of −0.08 to −0.03 as a calorific value equivalent coefficient $\zeta$; and a calorific value computation mechanism for computing a calorific value $Q$ [MJ/Nm$^3$] of the by-product gas by Equation (2) below using a value selected within a range of 1.1 to 4.2 as a correction factor $\alpha$ on the basis of the refractive index equivalent calorific value $Q_O$, the sonic speed equivalent calorific value $Q_S$ and the error calorific value $Q_{CO}$.

[Eq. 1]

$$Q_{CO} = X_{CO} \cdot \zeta \quad \text{Equation (1)}$$

$$Q = Q_0 - \frac{Q_0 - Q_S}{1-\alpha} - Q_{C0} \quad \text{Equation (2)}$$

In the calorific value measuring device of the present invention, the error calorific value measuring mechanism is preferably configured to include CO concentration measuring means for measuring the concentration of carbon monoxide gas contained in the by-product gas that is the calorific value measurement object gas.

In such a configuration, the CO concentration measuring means may preferably include an infrared sensor.

A calorific value measuring method of the present invention is to measure a calorific value of a by-product gas produced in a steelmaking process and characterized by including:

measuring a refractive index and a sonic speed of the by-product gas that is a calorific value measurement object gas and computing a refractive index equivalent calorific value $Q_O$ [MJ/Nm$^3$] from the value of the refractive index, and computing a sonic speed equivalent calorific value $Q_S$ [MJ/Nm$^3$] from the value of the sonic speed;

computing an error calorific value $Q_{CO}$ [MJ/Nm$^3$] by Equation (1) above using a value selected within a range of −0.08 to −0.03 as a calorific value equivalent coefficient $\zeta$ on the basis of the concentration $X_{CO}$ [vol % (volume percentage)] of carbon monoxide gas contained in the by-product gas; and determining a calorific value Q [MJ/Nm3] of the by-product gas by Equation (2) above using a value selected within a range of 1.1 to 4.2 as a correction factor $\alpha$ on the basis of the resulting refractive index equivalent calorific value $Q_O$, sonic speed equivalent calorific value $Q_S$ and error calorific value $Q_{CO}$.

Advantageous Effects of Invention

According to the calorific value measuring method of the present invention, the calorific value of the by-product gas can be measured with high reliability because the measurement errors of the refractive index equivalent calorific value and the sonic speed equivalent calorific value, which are caused by a miscellaneous gas contained in the by-product gas that is a calorific value measurement object gas, are compensated. As used herein, "the miscellaneous gas" refers to a gas component other than hydrogen gas and methane gas (paraffinic hydrocarbon gas) and thus includes, for example, carbon dioxide gas, carbon monoxide gas, nitrogen gas and oxygen gas.

According to the calorific value measuring device of the present invention in which such a calorific value measuring method is executed, it is possible to measure the calorific value of a by-product gas with high reliability. Furthermore, since the calorific value of a by-product gas can be continuously acquired corresponding to the actual situation, even in the case of a variation in gas composition, for example, when the concentration of carbon monoxide contained in a Linz-Donawitz converter gas is varied, it is possible to quickly detect the variation in calorific value that is caused by the variation in the gas composition.

DESCRIPTION OF EMBODIMENTS

Now, an embodiment of the present invention will be described in more detail below.

Figure 1:
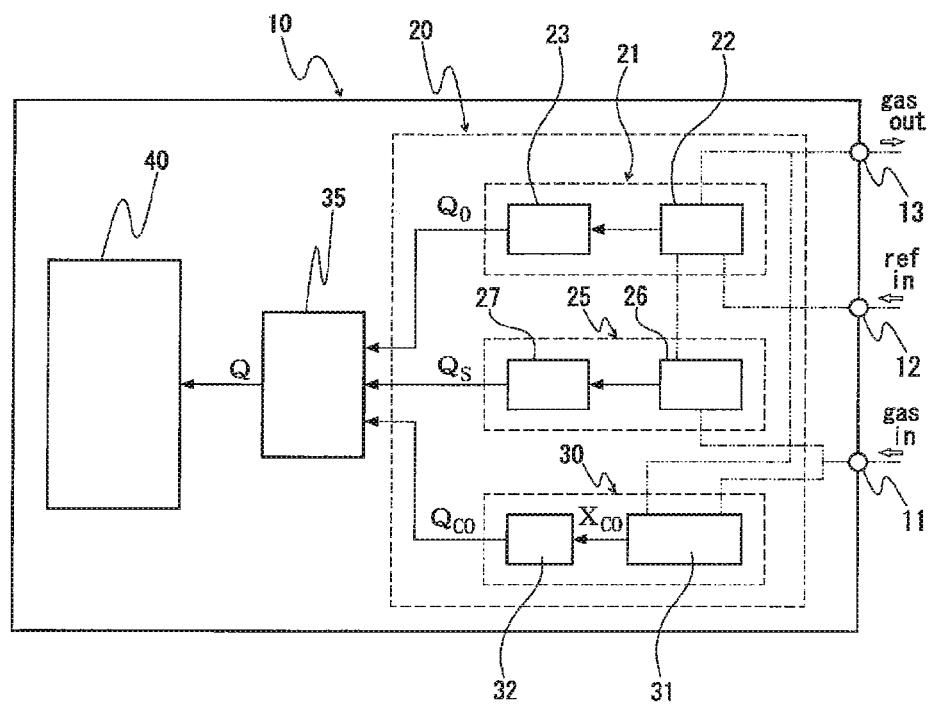
FIG. 1 is a block diagram schematically illustrating a configuration of an example of a calorific value measuring device of the present invention.

FIG. 1 is a block diagram schematically illustrating a configuration of an example of a calorific value measuring device of the present invention.

The calorific value measuring device employs, as a calorific value measurement object gas, a by-product gas such as a coke oven gas, a blast furnace gas and a Linz-Donawitz converter gas, produced in a steelmaking process. The calorific value measuring device is configured to include, a calorific value measuring mechanism 20 for measuring a calorific value of the calorific value measurement object gas and with a display mechanism 40 for displaying information such as the calorific value of the calorific value measurement object gas, which are arranged in a common outer container 10. Here, in the present invention, by setting as appropriate the correction factor and the calorific value equivalent coefficient as will be described later, it is possible to measure any of the total calorific value (Gross) and the true calorific value (Net), which hereafter, except when specified otherwise, will be referred to simply as "the calorific value."

The calorific value measuring mechanism 20 includes, for example: a refractive index equivalent calorific value measuring mechanism 21 for acquiring a refractive index equivalent calorific value $Q_O$ determined from the value of the refractive index of a calorific value measurement object gas; a sonic speed equivalent calorific value measuring mechanism 25 for acquiring a sonic speed equivalent calorific value $Q_S$ determined from the value of the sonic speed of the calorific value measurement object gas; an error calorific value measuring mechanism 30 for measuring an error calorific value $Q_{CO}$ caused by carbon monoxide gas on the basis of the concentration $X_{CO}$ [vol % (volume percentage)] of carbon monoxide gas contained in the calorific value measurement object gas; and a calorific value computation mechanism 35 for computing the value of the calorific value Q of the calorific value measurement object gas.

The refractive index equivalent calorific value measuring mechanism 21 include: refractive index measuring means 22 for measuring the refractive index of the calorific value measurement object gas; and refractive index—calorific value converting means 23 having a function of determining the refractive index equivalent calorific value $Q_O$ on the basis of the value of the refractive index measured by the refractive index measuring means 22.

Taking advantage of the correlation between the refractive index and the calorific value of a specific gas in the calorific value measurement object gas, which is acquired in advance, for example, by plotting a graph, the specific gas being computed of only a combustible gas component (paraffinic hydrocarbon gas) without any incombustible gas component, and assuming that the value of the refractive index acquired for the calorific value measurement object gas is the refractive index of the specific gas, the refractive index—calorific value converting means 23 computes the refractive index equivalent calorific value $Q_O$ by contrasting the value of the acquired refractive index with the correlation.

The sonic speed equivalent calorific value measuring mechanism 25 includes: sonic speed measuring means 26 for measuring the propagation speed of sound waves in the calorific value measurement object gas (the sonic speed of the calorific value measurement object gas); and sonic speed—calorific value converting means 27 having a function of determining the value of the sonic speed equivalent calorific value $Q_S$ on the basis of the value of the sonic speed measured by the sonic speed measuring means 26.

Taking advantage of the correlation between the sonic speed and the calorific value of a specific gas in the calorific value measurement object gas, which is acquired in advance, for example of only a combustible gas component (paraffinic hydrocarbon gas), by plotting a graph, the specific gas being composed without any incombustible gas component (for example, $N_2$), and assuming that the value of the sonic speed acquired for the calorific value measurement object gas is the sonic speed of the specific gas, the sonic speed—calorific value converting means 27 computes the sonic speed equivalent calorific value $Q_S$ by contrasting the value of the acquired sonic speed with the correlation.

The error calorific value measuring mechanism 30 includes, for example: CO concentration measuring means 31 for measuring the concentration of carbon monoxide gas contained in the calorific value measurement object gas; and CO concentration—calorific value converting means 32 for computing an error calorific value $Q_{CO}$ caused by the concentration of the carbon monoxide gas.

The CO concentration measuring means 31 is not limited to a particular one, but for example, may preferably be configured from one equipped with an infrared sensor for detecting the gas concentration of carbon monoxide gas depending on the level of attenuation of the quantity of infrared light caused by the infrared light being absorbed by carbon monoxide gas that is a gas to be sensed. Employing, as the CO concentration measuring means 31, one that takes advantage of a so-called non-dispersive infrared absorption method enables to make the influence of another miscellaneous gas contained in the calorific value measurement object gas as little as possible. This allows the concentration of carbon monoxide gas to be detected with high precision.

On the basis of the detected value of the concentration $X_{CO}$ [vol % (volume percentage)] of the carbon monoxide gas, the CO concentration—calorific value converting means 32 computes the error calorific value $Q_{CO}$ caused by the carbon monoxide gas by Equation (1) above under the condition of using a value selected within a range of −0.08 to −0.03 as the calorific value equivalent coefficient ζ.

Figure 2:
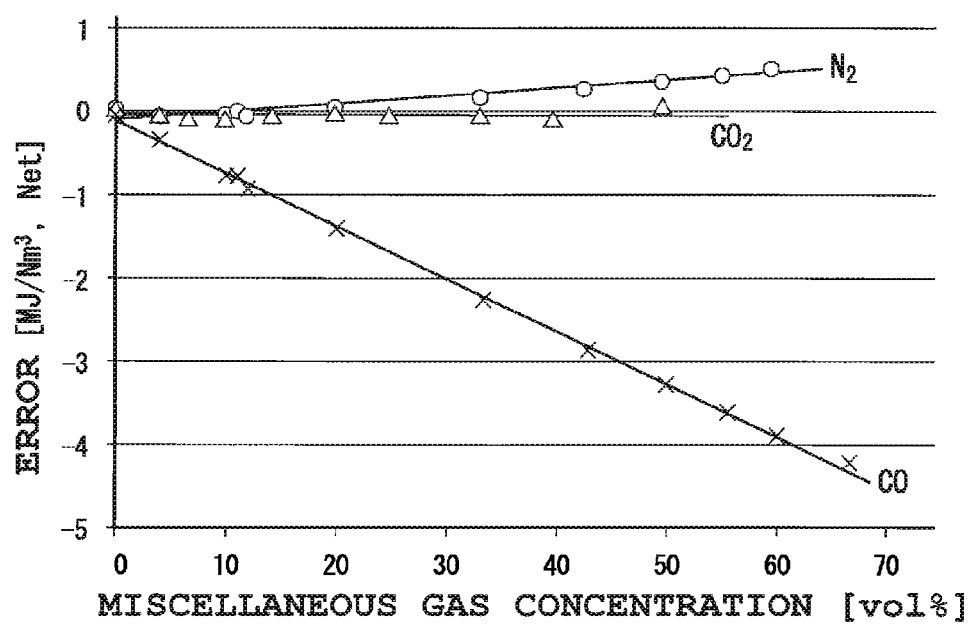
FIG. 2 is a graph indicative of the relation between the concentration of a miscellaneous gas and the error calorific value.

Equation (1) above was acquired as follows. That is, first, for each of multiple sorts of test gases, for example, predominantly composed of methane gas and having mutually different carbon monoxide gas concentrations, the true calorific value $Q_a$ of each test gas is computed with the error calorific value $Q_{CO}$ term being "0" in Equation (2) above under the condition of the correction factor α being 2.30, for example. Furthermore, for each of the test gases, the calorific value $Q_b$ is measured in conformity with JIS K2301: 2011. Then, for example, with the calorific value $Q_b$ acquired in conformity with JIS K2301:2011 being employed as a true value, the results are plotted (denoted by marking crosses) with the vertical axis representing the error [MJ/Nm$^3$, Net] to the true value of the calorific value $Q_a$ calculated under the aforementioned condition and the horizontal axis representing the concentration of carbon monoxide gas [vol % (volume percentage)]. FIG. 2 shows an example. As shown in FIG. 2, it is understood that the error calorific value caused by the carbon monoxide gas tends to increase in proportion to an increase in the concentration of the carbon monoxide gas. Thus, the linear approximation of the results of each test gas provides the approximate straight line expressed by Equation (1) above. That is, the gradient of the approximate straight line is set as the calorific value equivalent coefficient ζ. Then, since the calorific value equivalent coefficient ζ is a value selected within a range of −0.08 to −0.03, the error calorific value by the carbon monoxide gas can be computed with high precision irrespective of the sort of the calorific value measurement object gas.

Note that FIG. 2 shows a plot of data acquired by the same method as above for a test gas mixed with nitrogen gas or carbon dioxide gas in place of the carbon monoxide gas. It is understood that irrespective of the concentration of the nitrogen gas (plotted with circular marks) and the carbon dioxide gas (plotted with triangular marks), the influence of the error calorific value is substantially constant in magnitude, and the error calorific value itself has a magnitude that is substantially not problematic. Thus, the calorific value of the calorific value measurement object gas can be measured with high precision by taking into account the error calorific value caused by the carbon monoxide gas as the error calorific value exerting the influence on the sonic speed equivalent calorific value and the refractive index equivalent calorific value.

As an example of the calorific value equivalent coefficient ζ, to measure the total calorific value of the calorific value measurement object gas, the calorific value equivalent coefficient ζ can be set to −0.0475, for example. On the other hand, to measure the true calorific value of the calorific value measurement object gas, the calorific value equivalent coefficient ζ can be set to −0.0629, for example.

The calorific value computation mechanism 35 computes the value of the calorific value Q of the calorific value measurement object gas by Equation (2) above under the condition of using a value selected within a range of 1.1 to 4.2 as the correction factor α on the basis of the value of the refractive index equivalent calorific value $Q_O$ acquired by the refractive index equivalent calorific value measuring mechanism 21, the value of the sonic speed equivalent calorific value $Q_S$ acquired by the sonic speed equivalent calorific value measuring mechanism 25, and the value of the error calorific value $Q_{CO}$ caused by the carbon monoxide gas acquired by the error calorific value measuring mechanism 30.

The correction factor α is the value of the ratio of the measurement error in the sonic speed equivalent calorific value $Q_S$ caused by a miscellaneous gas being contained in the calorific value measurement object gas to the measurement error of the refractive index equivalent calorific value $Q_O$, and is selected corresponding to the composition of the calorific value measurement object gas.

In Equation (2) above, a value selected within a range of 1.1 to 4.2 is employed as the correction factor α, and in particular, a value selected within a range of 2.20 to 2.60 is preferably employed.

When the value of the correction factor α is excessively small, it is not possible to sufficiently correct the measurement errors occurring in the refractive index equivalent calorific value $Q_O$ and the sonic speed equivalent calorific value $Q_S$, so that the finally acquired value of the calorific value Q of the calorific value measurement object gas may have a measurement error caused by the miscellaneous gas being contained. On the other hand, when the value of the correction factor α is excessively large, the measurement errors occurring in the refractive index equivalent calorific value $Q_O$ and the sonic speed equivalent calorific value $Q_S$ may not be appropriately corrected, so that the finally acquired value of the calorific value Q of the calorific value measurement object gas may have a measurement error.

In the foregoing, a numeral 11 in FIG. 1 denotes a calorific value measurement object gas inlet for supplying the calorific value measurement object gas to each of the sonic speed measuring means 26, the refractive index measuring means 22 and the CO concentration measuring means 31; 12 denotes a reference gas inlet for introducing a reference gas required for the detection principle in the refractive index measuring means 22; and 13 denotes a gas exit unit. Furthermore, each of two-dot chain lines of FIG. 1 indicates a gas pipe.

In the aforementioned calorific value measuring device, a part of a by-product gas such as a coke oven gas, a blast furnace gas or a Linz-Donawitz converter gas is sequentially supplied, as the calorific value measurement object gas, from the calorific value measurement object gas inlet 11 to each of the sonic speed measuring means 26 of the sonic speed equivalent calorific value measuring mechanism 25 and the refractive index measuring means 22 of the refractive index equivalent calorific value measuring mechanism 21. Furthermore, for example, a reference gas such as air is supplied from the reference gas inlet 12 to the refractive index measuring means 22 of the refractive index equivalent calorific value measuring mechanism 21. In the sonic speed equivalent calorific value measuring mechanism 25, the sonic speed measuring means 26 measures the sonic speed of a by-product gas, and on the basis of the result, the value of the sonic speed equivalent calorific value $Q_S$ is determined by the sonic speed—calorific value converting means 27. Furthermore, in the refractive index equivalent calorific value measuring mechanism 21, the refractive index measuring means 22 measures the refractive index of the by-product gas, and on the basis of the result, the refractive index equivalent calorific value $Q_O$ is determined by the refractive index—calorific value converting means 23.

On the other hand, all the other part of the by-product gas introduced from the calorific value measurement object gas inlet 11 is supplied to the CO concentration measuring means 31 of the error calorific value measuring mechanism 30. In the error calorific value measuring mechanism 30, the CO concentration measuring means 31 measures the concentration $X_{CO}$ [vol % (volume percentage)] of carbon monoxide gas contained in the by-product gas. On the basis of the acquired value of the concentration $X_{CO}$ [vol % (volume percentage)] of the carbon monoxide gas, the error calorific value $Q_{CO}$ caused by the concentration of the carbon monoxide gas is determined by the CO concentration—calorific value converting means 32 by Equation (1) above under the condition of using a value selected within a specific range as the calorific value equivalent coefficient ζ.

On the basis of the value of the refractive index equivalent calorific value $Q_O$, the value of the sonic speed equivalent calorific value $Q_S$ and the value of the error calorific value $Q_{CO}$, which have been acquired as mentioned above, the calorific value Q of the by-product gas is computed by the calorific value computation mechanism 35 by Equation (2) above under the condition of using a value selected within a specific range as the correction factor α, and the result is displayed on the display mechanism 40.

Note that the by-product gas and the reference gas are discharged out of the device via the gas exit unit 13.

Then, as described above, when the calorific value of the by-product gas is measured on the basis of the refractive index equivalent calorific value $Q_O$ and the sonic speed equivalent calorific value $Q_S$, selecting only the value of the correction factor α expressed by the ratio of the measurement error of the sonic speed measuring means 26 to the measurement error of the refractive index measuring means 22 cannot compensate the measurement errors occurring in the refractive index equivalent calorific value $Q_O$ and the sonic speed equivalent calorific value $Q_S$, caused by a miscellaneous gas. The inventors have found the reason for this by focusing the influence by carbon monoxide gas as a miscellaneous gas contained in the by-product gas, i.e., it was found that other miscellaneous gases such as nitrogen gas and carbon dioxide gas have substantially a constant magnitude in the error calorific value even when the concentrations of these gases are changed, whereas the error calorific value due to the carbon monoxide gas is changed proportionally in relation to the concentration of the carbon monoxide gas. Then, it was found that the calorific value of the by-product gas can be measured with high precision by making a correction depending on the concentration $X_{CO}$ [vol % (volume percentage)] of the carbon monoxide gas.

Thus, according to the aforementioned calorific value measuring method, it is possible to compute, on the basis of the result acquired by measuring the concentration $X_{CO}$ [vol % (volume percentage)] of the carbon monoxide gas contained in the by-product gas, by Equation (1) above, the error calorific value $Q_{CO}$ caused by the concentration $X_{CO}$ [vol % (volume percentage)] of the carbon monoxide gas under the condition of using a value selected within a specific range as the calorific value equivalent coefficient ζ. As a result, compensated are the measurement errors of the refractive index equivalent calorific value $Q_O$ and the sonic speed equivalent calorific value $Q_S$ caused by the miscellaneous gas of carbon monoxide gas and other gases contained in the by-product gas, that is the calorific value measurement object gas. It is thus possible to measure the calorific value Q of the by-product gas with high reliability.

Then, according to the calorific value measuring device of the present invention in which such a calorific value measuring method is executed, the calorific value Q of the by-product gas can be measured with high reliability. Furthermore, since the calorific value Q of the by-product gas can be continuously acquired corresponding to the actual situation, it is possible to immediately detect a variation in the calorific value Q resulting from a variation in gas composition even in the presence of the variation in the gas composition, for example, even in the occurrence of a variation in the concentration of carbon monoxide gas contained in the Linz-Donawitz converter gas.

Furthermore, the aforementioned calorific value measuring device is configured such that multiple sorts of measuring means (sensors) which constitute the calorific value measuring mechanism 20, having mutually different detection principles, such as the refractive index equivalent calorific value measuring mechanism 21, the sonic speed equivalent calorific value measuring mechanism 25 and the error calorific value measuring mechanism 30, are provided in the common outer container 10. This simplifies the construction and operation of the measurement system. Furthermore, since not much time is required for measurement, and no time lags are accompanied for computations of the refractive index equivalent calorific value $Q_O$ and the sonic speed equivalent calorific value $Q_S$ as well as and the error calorific value $Q_{CO}$, it is possible to measure the calorific value Q of the by-product gas in real time.

In the foregoing, the embodiment of the present invention has been described. However, the present invention is not limited to the aforementioned embodiment, but various modifications may be made thereto.

For example, the CO concentration measuring means in the error calorific value measuring mechanism is not limited to one that takes advantage of a so-called non-dispersive infrared absorption method, but may also be provided with another gas sensor that is capable of detecting the concentration of the carbon monoxide gas. Furthermore, the calorific value measuring device itself is not required to include the CO concentration measuring means, but may also be configured to allow an appropriate CO concentration measuring device to measure the concentration of carbon monoxide gas contained in the calorific value measurement object gas and then the concentration data thus acquired to be inputted.

Now, example experiments of the present invention will be described below.

Example Experiment 1

As test gases, a coke oven gas (COG), a blast furnace gas (BFG) and a Linz-Donawitz converter gas (LDG) that had the compositions shown in Table 1 below were prepared.

For each of these three sorts of test gases, the refractive index, the sonic speed (density) and the concentration of carbon monoxide gas were measured using a gas refractometer with a refractive index sensor, a gas densimeter with a sonic speed sensor and a gas concentration meter with an infrared sensor, respectively.

Figure 3:
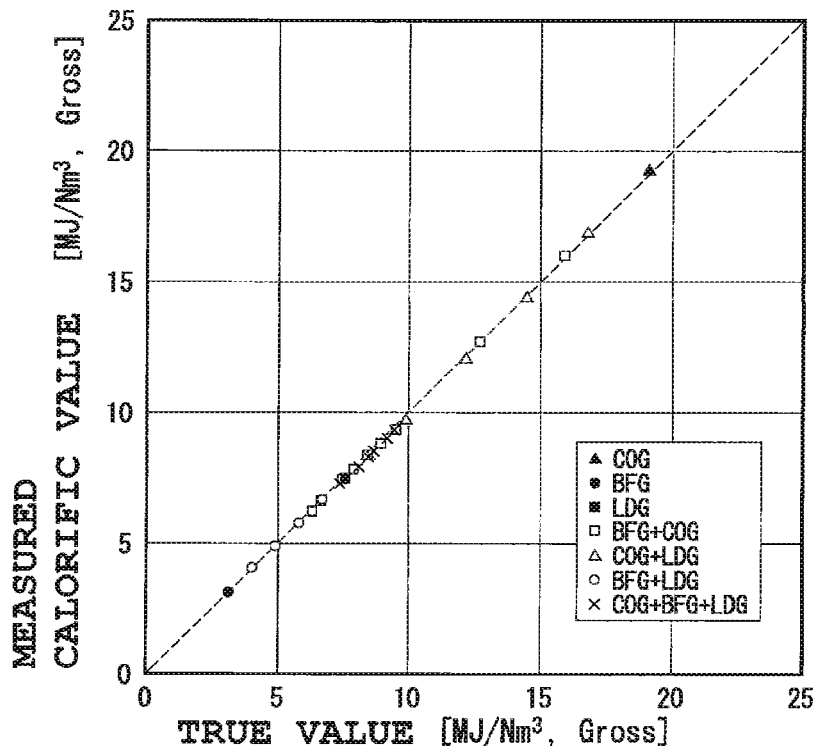
FIG. 3 is a graph indicative of the relation, for each test gas used in an example experiment, between the value of a calorific value acquired by a calorific value measuring method according to the present invention and the value of a calorific value acquired in conformity with JIS K2301: 2011.

On the basis of the acquired values of the refractive index, the sonic speed and the concentration value of the carbon monoxide gas, the value of the total calorific value of each test gas was computed by Equation (1) and Equation (2) above, where the correction factor $\alpha$ was 2.27 and the calorific value equivalent coefficient was −0.0475. Then, with the value of the calorific value acquired in conformity with JIS K2301:2011 being a true value, the relation between the measured value of the calorific value (measured calorific value) and the true value was examined. The results of the coke oven gas (COG), the blast furnace gas (BFG) and the Linz-Donawitz converter gas (LDG) are denoted in FIG. 3 by a filled triangular plot (▲), a filled circular plot (●) and a filled square plot (■), respectively. Here, in FIG. 3, the horizontal axis represents the calorific value as the true value and the vertical axis represents the measured calorific value. Furthermore, the straight line denoted by a broken line is an ideal curved line with the error between the measured value of calorific value and the true value being zero.

TABLE 1

| | COMPOSITION [vol %] | | | | |
|---|---|---|---|---|---|
| | $N_2$ | CO | $CO_2$ | $CH_4$ | $H_2$ |
| COG | 5.03 | 7.48 | 3.49 | 27.44 | 56.56 |
| BFG | 55.00 | 21.98 | 20.52 | 0 | 2.50 |
| LDG | 21.49 | 58.50 | 18.51 | 0 | 1.50 |

Example Experiment 2

As test gases, used were multiple sorts of gases which were mixture gases (M gases) prepared by mixing the aforementioned coke oven gas (COG) and the aforementioned blast furnace gas (BFG) with appropriately varied mixing ratios of the coke oven gas (COG) and the blast furnace gas (BFG). Except for this, the same method as that of Example Experiment 1 was followed to measure the total calorific value of each test gas. Then, with the value of calorific value acquired in conformity with JIS K2301:2011 being employed as a true value, the relation between the measured calorific value and the true value was examined. The results are denoted in FIG. 3 by hollow square plots (□):

Example Experiment 3

As test gases, used were multiple sorts of gases which were mixture gases (M gases) prepared by mixing the aforementioned coke oven gas (COG) and the aforementioned Linz-Donawitz converter gas (LDG) with appropriately varied mixing ratios of the coke oven gas (COG) and the Linz-Donawitz converter gas (LDG). Except for this, the same method as that of Example Experiment 1 was followed to measure the total calorific value of each test gas. Then, with the value of the calorific value acquired in conformity with JIS K2301:2011 being employed as a true value, the relation between the measured calorific value and the true value was examined. The results are denoted in FIG. 3 by hollow triangular plots (▲).

Example Experiment 4

As test gases, used were multiple sorts of gases which were mixture gases (N gases) prepared by mixing the aforementioned blast furnace gas (BFG) and the aforementioned Linz-Donawitz converter gas (LDG) with appropriately varied mixing ratios of the blast furnace gas (BFG) and the Linz-Donawitz converter gas (LDG). Except for this, the same method as that of Example Experiment 1 was followed to measure the total calorific value of each test gas. Then, with the value of the calorific value acquired in conformity with JIS K2301:2011 being employed as a true value, the relation between the measured calorific value and the true value was examined. The results are denoted in FIG. 3 by hollow circular plots (o).

Example Experiment 5

As test gases, used were multiple sorts of gases which were mixture gases (M gases) prepared by mixing the aforementioned coke oven gas (COG), the aforementioned blast furnace gas (BFG) and the aforementioned Linz-Donawitz converter gas (LDG) with appropriately varied mixing ratios of the coke oven gas (COG), the blast furnace gas (BFG) and the Linz-Donawitz converter gas (LDG). Except for this, the same method as that of Example Experiment 1 was followed to measure the total calorific value of each test gas. Then, with the value of the calorific value acquired in conformity with JIS K2301:2011 being employed as a true value, the relation between the measured calorific value and the true value was examined. The results are denoted in FIG. 3 by cross plots (x).

Comparative Example Experiments 1 to 5

Figure 4:
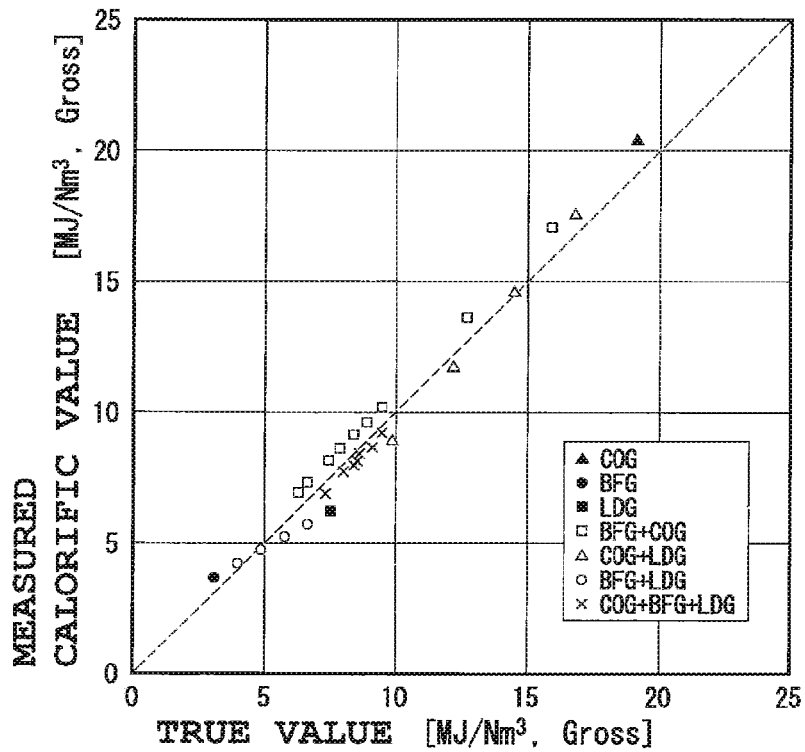
FIG. 4 is a graph indicative of the relation, for each test gas used in a comparative example experiment, between the value of a calorific value acquired when no correction was made to carbon monoxide gas and the value of a calorific value acquired in conformity with JIS K2301:2011.

To each of the plurality of test gases employed in Example Experiment 1 to Example Experiment 5, no correction was made by the concentration of carbon monoxide gas contained in the test gas ($Q_{CO}$=0 in Equation (1) above). Except for this, the same method as that of Example Experiment 1 was followed to measure the total calorific value of each test gas. Then, with the value of the calorific value acquired in conformity with JIS K2301:2011 being employed as a true value, the relation between the measured calorific value and the true value was examined. The results are shown in FIG. 4.

As can be seen clearly from the results above, in Example Experiment 1 to Example Experiment 5, it was confirmed that the calorific value (total calorific value) of the test gas could be measured with high precision by making a correction depending on the concentration of the carbon monoxide gas contained in the test gas. In contrast to this, for Comparative Example Experiment 1 to Comparative Example Experiment 5, it was confirmed that due to the influence of the carbon monoxide gas, there occurred a measurement error at a level that could not be practically neglected.

REFERENCE SIGNS LIST 10 outer container
11 calorific value measurement object gas inlet
12 reference gas inlet
13 gas exit unit
20 calorific value measuring mechanism
21 refractive index equivalent calorific value measuring mechanism
22 refractive index measuring means
23 refractive index—calorific value converting means
25 sonic speed equivalent calorific value measuring mechanism
26 sonic speed measuring means
27 sonic speed—calorific value converting means
30 error calorific value measuring mechanism
31 CO concentration measuring means
32 CO concentration—calorific value converting means
35 calorific value computation mechanism
40 display mechanism

The invention claimed is:

1. A calorific value measuring device for measuring a calorific value of a by-product gas produced in a steelmaking process, the calorific value measuring device comprising:
a refractive index equivalent calorific value computation mechanism for computing a refractive index equivalent calorific value $Q_O$ [MJ/Nm$^3$] based on a refractive index of a by-product gas that is a calorific value measurement object gas;
a sonic speed equivalent calorific value computation mechanism for computing a sonic speed equivalent calorific value $Q_S$ [MJ/Nm$^3$] based on a sonic speed of the by-product gas;
an error calorific value measuring mechanism for computing an error calorific value $Q_{co}$ [MJ/Nm$^3$] exerting an influence on the sonic speed equivalent calorific value and the refractive index equivalent calorific value based on a first equation expressed as
$Q_{co} = X_{co} \zeta$,
wherein $X_{co}$ represents a concentration [vol % (volume percentage)] of carbon monoxide gas contained in the by-product gas and $\zeta$ is a calorific value equivalent coefficient having a value selected within a range of −0.08 to −0.03; and
a calorific value computation mechanism for computing a calorific value $Q$ [MJ/Nm$^3$] of the by-product gas based on a second equation expressed as $$Q = Q_0 - \frac{Q_0 - Q_S}{1 - \alpha} - Q_{C0},$$

wherein $\alpha$ is a correction factor having a value selected within a range of 1.1 to 4.2 based on the refractive index equivalent calorific value $Q_O$, the sonic speed equivalent calorific value $Q_S$ and the error calorific value $Q_{co}$.

2. The calorific value measuring device according to claim 1, wherein the error calorific value measuring mechanism includes CO concentration measuring means for measuring a concentration of carbon monoxide gas contained in the by-product gas that is the calorific value measurement object gas.

3. The calorific value measuring device according to claim 2, wherein the CO concentration measuring means includes an infrared sensor.

4. A calorific value measuring method for measuring a calorific value of a by-product gas produced in a steelmaking process, the calorific value measuring method comprising:
measuring a refractive index and a sonic speed of the by-product gas that is a calorific value measurement object gas and computing a refractive index equivalent calorific value $Q_O$ [MJ/Nm$^3$] from a value of the refractive index, and computing a sonic speed equivalent calorific value $Q_S$ [MJ/Nm$^3$] from a value of the sonic speed;
computing an error calorific value $Q_{co}$ [MJ/Nm$^3$] exerting an influence on the sonic speed equivalent calorific value and the refractive index equivalent calorific value based on a first equation expressed as
$Q_{co} = X_{co} \zeta$,
wherein $\zeta$ is a calorific value equivalent coefficient having a value selected within a range of −0.08 to −0.03 and $X_{co}$ represents a concentration [vol % (volume percentage)] of carbon monoxide gas contained in the by-product gas; and
determining a calorific value $Q$ [MJ/Nm$^3$] of the by-product gas based on a second equation expressed as $$Q = Q_0 - \frac{Q_0 - Q_S}{1 - \alpha} - Q_{C0},$$

wherein $\alpha$ is a correction factor having a value selected within a range of 1.1 to 4.2 based on the resulting refractive index equivalent calorific value $Q_O$, sonic speed equivalent calorific value $Q_S$ and error calorific value $Q_{co}$.

* * * * *